(12) United States Patent
Shi et al.

(10) Patent No.: US 11,692,935 B2
(45) Date of Patent: Jul. 4, 2023

(54) TRANSIENT-STATE THZ SPECTROMETER FOR DETECTING CELLS AND BIOLOGICAL MACROMOLECULES

(71) Applicant: XI'AN UNIVERSITY OF TECHNOLOGY, Shanxi (CN)

(72) Inventors: Wei Shi, Shanxi (CN); Lei Hou, Shanxi (CN); Cheng Ma, Shanxi (CN); Chengang Dong, Shanxi (CN); Lei Yang, Shanxi (CN); Jiaguang Han, Shanxi (CN); Yanfeng Li, Shanxi (CN); Chunmei Ouyang, Shanxi (CN); Jianqiang Gu, Shanxi (CN); Liguo Zhu, Shanxi (CN); Zhaohui Zhai, Shanxi (CN); Lianghui Du, Shanxi (CN); Yi Zou, Shanxi (CN)

(73) Assignee: XI'AN UNIVERSITY OF TECHNOLOGY, Shaanxi (CN)

( * ) Notice: Subject to any disclaimer, the term of this patent is extended or adjusted under 35 U.S.C. 154(b) by 0 days.

(21) Appl. No.: 17/276,825

(22) PCT Filed: Jan. 13, 2021

(86) PCT No.: PCT/CN2021/071584
§ 371 (c)(1),
(2) Date: Mar. 17, 2021

(87) PCT Pub. No.: WO2021/227547
PCT Pub. Date: Nov. 18, 2021

(65) Prior Publication Data
US 2023/0058188 A1   Feb. 23, 2023

(30) Foreign Application Priority Data
May 15, 2020 (CN) .......... 202010412903.6

(51) Int. Cl.
*G01N 21/3581* (2014.01)
*G01N 21/3577* (2014.01)
(Continued)

(52) U.S. Cl.
CPC ..... *G01N 21/3581* (2013.01); *G01N 21/3577* (2013.01); *G01N 21/39* (2013.01);
(Continued)

(58) Field of Classification Search
CPC .......... G01N 21/3581; G01N 21/3577; G01N 21/39; G01N 33/48721; G01N 2021/177;
(Continued)

(56) References Cited

U.S. PATENT DOCUMENTS

2008/0239317 A1* 10/2008 Schulkin ................. H01S 5/023
356/365
2009/0303574 A1* 12/2009 Gunter .................. G02F 1/3515
359/328
(Continued)

FOREIGN PATENT DOCUMENTS

CN    204346910 U    5/2015
CN    105675536 A    6/2016
(Continued)

OTHER PUBLICATIONS

Li et al., "Non-linear model of photoconductive antenna", Chinese Physics Letters, vol. 30, No. 6, pp. 064102-1 to 064102-4. (Year: 2013).*
(Continued)

*Primary Examiner* — Kiho Kim
(74) *Attorney, Agent, or Firm* — Gang Yu

(57) ABSTRACT

Disclosed is a transient-state THz spectrometer applied to cells and biological macromolecules, including a femtosecond laser amplifier. A femtosecond laser output by the femtosecond laser amplifier is divided into two beams of
(Continued)

pump light and probe light after passing through a beam splitter of which a transmission-reflection ratio is 7:3, the pump light is focused to irradiate a gap between electrodes of a nonlinear photoconductive antenna and emit a terahertz wave after successively passing through a half wave plate, a silver-plated reflector and a first lens, the terahertz wave forms a terahertz wave collineation after successively passing through a second lens, a slab waveguide, a third lens and an ITO film, the terahertz wave collineation and the probe light form a probe light collineation of wavefront tilt which is perpendicularly incident on a ZnTe crystal and detected and recorded by using a CCD camera.

20 Claims, 2 Drawing Sheets

(51) Int. Cl.
  *G01N 21/39* (2006.01)
  *G01N 33/487* (2006.01)
  *G01N 21/17* (2006.01)
(52) U.S. Cl.
  CPC . *G01N 33/48721* (2013.01); *G01N 2021/177* (2013.01); *G01N 2021/396* (2013.01)
(58) Field of Classification Search
  CPC ......... G01N 2021/396; G01N 21/3586; G01N 21/01; G01N 2201/06; G01N 2201/08
  See application file for complete search history.

(56) References Cited

U.S. PATENT DOCUMENTS

| | | | |
|---|---|---|---|
| 2010/0288928 A1* | 11/2010 | Katagiri | G01J 11/00 250/340 |
| 2014/0264032 A1* | 9/2014 | Neshat | G01J 3/42 250/339.08 |
| 2015/0015890 A1* | 1/2015 | Zheng | G01J 3/10 356/450 |
| 2016/0202179 A1* | 7/2016 | Nakanishi | G01N 21/3563 250/352 |
| 2017/0336482 A1* | 11/2017 | Hwang | G01R 33/60 |

FOREIGN PATENT DOCUMENTS

| | | |
|---|---|---|
| CN | 108020525 A | 5/2018 |
| CN | 109781656 A | 5/2019 |
| CN | 111537466 A | 8/2020 |
| WO | 2004106900 A1 | 12/2004 |

OTHER PUBLICATIONS

Yang, Lei et al. "Single-Shot Measurement of Terahertz Pulses Based onTilted Wavefront". Chinese Journal of Lasers. vol. 46, No. 6. pp. 0614028-1-6.

Jiangquan Zhang et al. "Adiabatic compression of parallel-plate metal waveguides for sensitivity enhancement of waveguide THz time-domain spectroscopy". Applied Physics Letters. vol. 86, 061109. pp. 1-3.

International Search Report for corresponding application PCT/CN2021/071584 filed Jan. 13, 2021; dated Apr. 19, 2021.

* cited by examiner

TRANSIENT-STATE THZ SPECTROMETER FOR DETECTING CELLS AND BIOLOGICAL MACROMOLECULES

TECHNICAL FIELD

The disclosure belongs to the field of biomedical substance identification and detection, and particularly relates to a transient-state THz spectrometer for detecting cells and biological macromolecules.

BACKGROUND

A terahertz wave usually refers to electromagnetic radiation of which a frequency is within a range of 0.1 THz to 10 THz (a wavelength is in 3 mm to 30 μm). Compared with other wavebands, the terahertz wave has (1) low energy while being used in biomedical detection: the energy thereof is a millielectron volt, it may not cause harmful photoionization to a biological tissue; (2) transient performance: a typical pulse width of a terahertz pulse is in an order of picoseconds, it may show a rapid change process of a biological substance in the order of the picoseconds; and (3) fingerprint characteristics: vibration and rotation energy levels of most biomolecules are located in a terahertz frequency band, so the terahertz wave is used to detect and analyze the biological substance, and to research constituents, molecular structures and physical and chemical properties of the substances to be detected, because it has unique characteristics similar to a fingerprint, it is also called as a molecular fingerprint spectrum. Therefore, compared with other chemical detection methods (such as a kit method, and a mass spectrometry), terahertz transient-state spectroscopy detection is an important detection method.

At present, most of work that is carried out at home and abroad is carried out in a terahertz time domain spectroscopy system (THz-TDS) in a traditional free space, it may not meet the needs of transient-state dynamics researches on water-containing low-concentration biological samples, because they may not achieve a single measurement, and are limited by a diffraction limit of free-space light, they may not perform fine measurements on smaller-sized samples, and are affected by water absorption in cells and biological macromolecules.

In order to solve the above problems, the present application couples the terahertz waves in the free space into modes such as an evanescent wave, a waveguide wave or pseudo surface plasmons, an evanescent field or local field enhancement effect thereof is used to achieve detection of trace cells or biological macromolecules, and at the same time, the coupling efficiency is guaranteed to meet a transient dynamics research.

SUMMARY

A purpose of the disclosure is to provide a transient-state THz spectrometer for detecting cells and biological macromolecules, not only a single measurement may be performed, but also a transient-state detection of a water-containing biological sample in a femtomolar level may be achieved.

According to one aspect of the disclosure, a transient-state THz spectrometer for detecting cells and biological macromolecules is provided, and comprises a femtosecond laser amplifier, a femtosecond laser output by the femtosecond laser amplifier is divided into two beams of pump light and probe light after passing through a beam splitter of which a transmission-reflection ratio is 7:3, the pump light is focused to irradiate a gap between electrodes of a nonlinear photoconductive antenna and emit a terahertz wave after successively passing through a half wave plate, a silver-plated reflector and a first lens, the obtained terahertz wave forms a terahertz wave collineation after successively passing through a second lens, a slab waveguide, a third lens and an ITO film, the terahertz wave collineation and the probe light form a probe light collineation of wavefront tilt which is perpendicularly incident on a ZnTe crystal and detected and recorded by using a CCD camera.

Features of a technical scheme adopted in the disclosure are as follows.

The probe light obtained by the beam splitter successively passes through a blazed grating and a silver-plated reflector and is reflected to a first polarizer, and then focused by a fourth lens and passes through the ITO film to form a probe light collineation of wavefront tilt, and an angle of the blazed grating is 66.44° deviated from a vertical direction.

One side, away from the ITO film, of the ZnTe crystal is successively provided with a quarter wave plate, a fifth lens and a second polarizer, the probe light amplified by the fifth lens passes through the second polarizer and is imaged to the CCD camera.

A line density of the blazed grating is 1200 lines/mm, and a blaze wavelength is 800 nm.

The slab waveguide is a horn-like structure made of an oxygen-free copper metal material.

The slab waveguide comprises axial-symmetrically arranged slab upper waveguide and slab lower waveguide, the gap between the slab upper waveguide and the slab lower waveguide d=50 μm-400 μm, the gap of the slab lower waveguide is provided with a pseudo surface plasmon chip, the slab upper waveguide, the slab lower waveguide and the pseudo surface plasmon chip loaded in the gap of the slab lower waveguide form a horn-like gradient structure together.

An overall length of the slab waveguide $l1$=210 mm-310 mm, a distance from an upper edge of a horn port of the horn-like gradient structure to an upper edge of the slab waveguide $l2$=2 mm-2.5 mm, a propagation length of the slab waveguide $l3$=10 mm-20 mm, a distance from a lower edge of the horn port of the horn-like gradient structure to an upper edge of the slab waveguide $l4$=5 mm-10 mm, a smooth change trend of the horn port α=0.0125 mm-0.02 mm, and two end points of the horn port are respectively (x1, y1) and (x2, y2), it is set (x1, y1)=(0, 0); then (x2, y2)=(($l1$−$l3$)/2, $l4$).

An opening width of a grating of the pseudo surface plasmon chip α=15 μm-40 μm, a period of the grating p=30 μm-80 μm, and an opening depth of the grating h=15 μm-40 μm.

The femtosecond laser amplifier is a Ti sapphire regenerative amplifier Spitfire Ace, a laser repetition frequency thereof is 1 Hz-1000 Hz, average power is 5 W, and a pulse width is 100 fs.

The horn-like gradient structure may transform the terahertz wave in the free space into a TEM mode propagated in the slab waveguide, and the coupling efficiency thereof is 80.5%.

According to another aspect of the disclosure, a transient-state THz spectrometer for detecting cells and biological macromolecules is provided, comprising:

a femtosecond laser amplifier, used to output a femtosecond laser;

a beam splitter, used to divide the femtosecond laser into two beams of pump light and probe light;

a half wave plate, a silver-plated reflector, a first lens and a nonlinear photoconductive antenna, herein the first lens is used to focus the pump light successively passing through the half wave plate and the silver-plated reflector to irradiate a gap between electrodes of the nonlinear photoconductive antenna, and the nonlinear photoconductive antenna is used to emit a terahertz wave;

a second lens, a slab waveguide, a third lens and an ITO film, used to form a terahertz wave and probe light collineation after enabling the terahertz wave to successively pass and perpendicularly incident on a ZnTe crystal; and a CCD camera, used to detect and record the probe light incident on the ZnTe crystal and carrying information of the terahertz wave.

Further, the above transient-state THz spectrometer further comprises:

a blazed grating, a silver-plated reflector, a first polarizer and a fourth lens, the silver-plated reflector is used to reflect the probe light passing through the blazed grating to the first polarizer, the fourth lens is used to focus the probe light passing through the first polarizer, the ITO film is used to enable the focused probe light to pass and reflect the terahertz wave so as to form the probe light of wavefront tilt which is collinear with the terahertz wave, and an angle of the blazed grating is 66.44° deviated from a vertical direction.

Further, the above transient-state THz spectrometer further comprises a quarter wave plate, a fifth lens and a second polarizer, the quarter wave plate, the fifth lens and the second polarizer are disposed at one side, away from the ITO film, of the ZnTe crystal and successively arranged along a direction away from the ITO film, the fifth lens is used to beam-expand the passing probe light, and the beam-expanded probe light is imaged to the CCD camera after passing through the second polarizer.

Further, a line density of the above blazed grating is 1200 lines/mm, and a blaze wavelength is 800 nm.

Further, the above slab waveguide is a horn-like structure made of an oxygen-free copper metal material.

Further, the above slab waveguide comprises axial-symmetrically arranged slab upper waveguide and slab lower waveguide, a gap between the slab upper waveguide and the slab lower waveguide d=50 µm-400 µm, a surface, located at the gap, of the slab lower waveguide is provided with a pseudo surface plasmon chip, the slab upper waveguide, the slab lower waveguide and the pseudo surface plasmon chip loaded in the gap form a horn-like gradient structure together.

Further, an overall length of the above slab waveguide l1=210 mm-310 mm, a distance from an upper edge of a horn port of the horn-like gradient structure to an upper edge of the slab waveguide l2=2 mm-2.5 mm, a propagation length of the slab waveguide l3=10 mm-20 mm, a distance from a lower edge of the horn port of the horn-like gradient structure to an upper edge of the slab waveguide l4=5 mm-10 mm, a smooth change trend of the horn port α=0.0125 mm-0.02 mm, and two end points of the horn port are respectively (x1, y1) and (x2, y2), it is set (x1, y1)=(0, 0); then (x2, y2)=((l1−l3)/2, l4).

Further, an opening width of a grating of the above pseudo surface plasmon chip α=15 µm-40 µm, a period of the grating p=30 µm-80 µm, and an opening depth of the grating h=15 µm-40 µm.

Further, the above femtosecond laser amplifier is a Ti sapphire regenerative amplifier, a laser repetition frequency thereof is 1 Hz-1000 Hz, average power is 5 W, and a pulse width is 100 fs.

Further, the above horn-like gradient structure is used to transform the terahertz wave in the free space into a TEM mode propagated in the slab waveguide, and the coupling efficiency thereof is 80.5%.

The beneficial effects of the disclosure are as follows: the transient-state THz spectrometer of the disclosure is required to have characteristics such as short detection time, reduced influence of water absorption in a sample to be detected and high detection accuracy. The disclosure is capable of, (1) in order to shorten the detection time, constructing a set of a terahertz pulse single measurement system based on a grating inclination laser wavefront technology, herein the nonlinear photoconductive antenna is mainly used as a terahertz high-power radiation source, the CCD camera is used to receive single probe light containing the terahertz wave information so as to achieve the single measurement, and the detection may be completely only if one terahertz pulse containing the biological sample to be detected is detected; (2) coupling the terahertz wave in the free space into the oxygen-free copper metal slab waveguide by using the horn-like gradient waveguide, and increasing the local field strength in the waveguide; and (3) in order to reduce the influence of the water absorption in the sample to be detected, coupling the terahertz wave in the metal slab waveguide into the pseudo surface plasmons by using the pseudo surface plasmon waveguide, using the evanescent field or local field enhancement effect thereof to achieve the detection of the trace cells or biological macromolecules, and at the same time, guaranteeing the coupling efficiency to meet the research of the transient dynamics. Finally, through a design of the transient-state THz spectrometer applied to the cells and biological macromolecules, a transient-state detection of a water-containing biological sample in a femtomolar level is achieved.

Herein, 1. Femtosecond laser amplifier, 2. Beam splitter, 3. Half wave plate, 4. Silver-plated reflector, 5. First lens, 6. Non-linear photoconductive antenna, 7. Second lens, 8. Slab waveguide, 9. Third lens, 10. Blazed grating, 11. Silver-plated reflector, 12. First polarizer, 13. Fourth lens, 14. ITO film, 15. ZnTe crystal, 16. Quarter wave plate, 17. Fifth lens, 18. Second polarizer, 19. CCD camera, 20. Slab upper waveguide, 21. Slab lower waveguide, 22. Horn-like gradient structure, and 23. Pseudo surface plasmon chip.

DETAILED DESCRIPTION OF THE EMBODIMENTS

The disclosure is further described below according to drawings and specific implementation modes.

Figure 1:
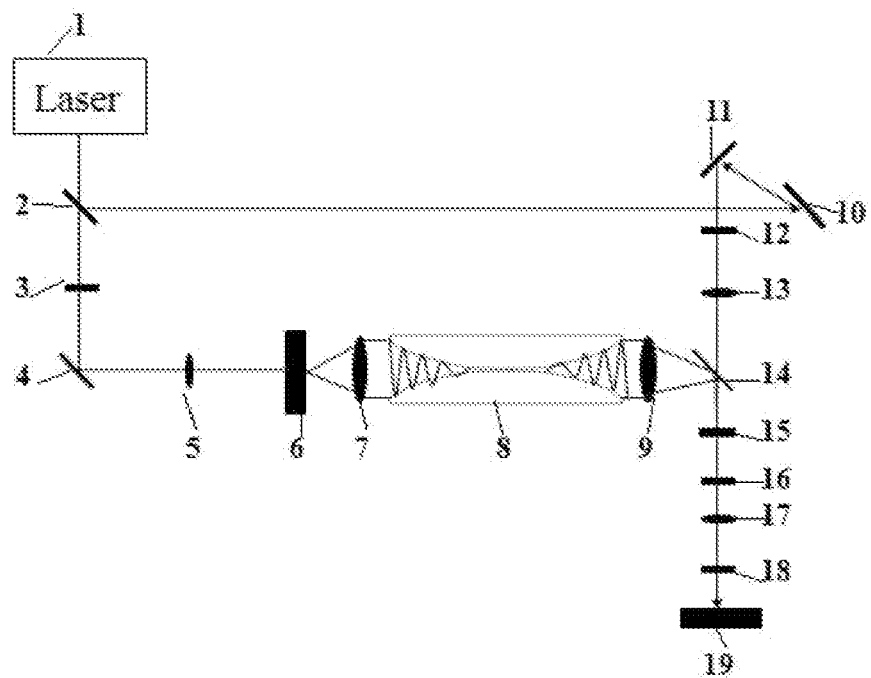
FIG. 1 is a schematic diagram of a terahertz pulse single measurement system in a transient-state THz spectrometer for detecting cells and biological macromolecules of the disclosure.

As shown in FIG. 1, it is a structure schematic diagram of a transient-state THz spectrometer for detecting cells and biological macromolecules of the disclosure, including a femtosecond laser amplifier 1, a femtosecond laser output by the femtosecond laser amplifier 1 is divided into two beams of pump light and probe light after passing through a beam splitter 2 of which a transmittance-reflection ratio is 7:3, herein the pump light is focused to irradiate a gap between electrodes of the nonlinear photoconductive antenna 6 after successively passing through a half wave plate 3, a silver-plated reflector 4 and a first lens 5 so as to radiate a terahertz wave, the terahertz wave enters a horn-like oxygen-free copper metal slab waveguide 8 after passing through a second lens 7 so as to form a local field enhancement effect at a waveguide gap, and finally forms a terahertz wave collineation after passing through a third lens 9 and an ITO film 14; the probe light obtained by the beam splitter 2 is firstly diffracted by a blazed grating 10, an angle of the blazed grating 10 is 66.44° deviated from a vertical direction, after diffraction, a front edge of a probe light pulse is inclined, the inclined probe light is reflected by a silver-plated reflector 11 to a first polarizer 12, and then focused by a fourth lens 13 and passes through the ITO film 14 to form the probe light of wavefront tilt, the terahertz wave and the probe light are collinear and are perpendicularly incident on a ZnTe crystal 15 together, a polarization state of the probe light is changed along with modulation of a terahertz electric field. One side, away from the ITO film 14, of the ZnTe crystal 15 is successively provided with a quarter wave plate 16, a fifth lens 17, and a second polarizer 18. The probe light passes through the quarter wave plate 16 and the second polarizer 18 to analyze the polarization state of the probe light, and the probe light is beam-expanded by the fifth lens 17, and imaged to a CCD camera 19 through the above quarter wave plate 16, fifth lens 17 and second polarizer 18, thereby an electric field modulation process of a single terahertz pulse is achieved by using one probe light pulse. It should be noted that the above fifth lens 17 may also be disposed on one side, away from the quarter wave plate 16, of the second polarizer 18, so the probe light sequentially passing through the quarter wave plate 16 and the second polarizer 18 is beam-expanded by the fifth lens 17 and imaged to the CCD camera 19.

The femtosecond laser amplifier 1 used in the disclosure is a Ti sapphire regenerative amplifier Spitfire Ace produced by Spectra-Physics Company, a laser repetition frequency thereof is 1 Hz to 1000 Hz, average power is 5 W, and a pulse width is 100 fs. A line density of the blazed grating 10 is 1200 lines/mm, and a blaze wavelength is 800 nm, a main function is to make the probe light generate the wavefront tilt and overlap with the terahertz wave, and then the CCD camera 19 is used to receive a single light pulse signal carrying terahertz information, the above terahertz information is information of the terahertz wave, and the above light pulse signal is a pulse signal of the probe light incident on the ZnTe crystal. At the same time, because own software of the CCD camera 19 has a background subtraction function, an effect caused by a background noise in a terahertz pulse single measurement may be eliminated, and a signal-to-noise ratio of the spectrometer of the disclosure is higher than 1000:1.

Figure 2:
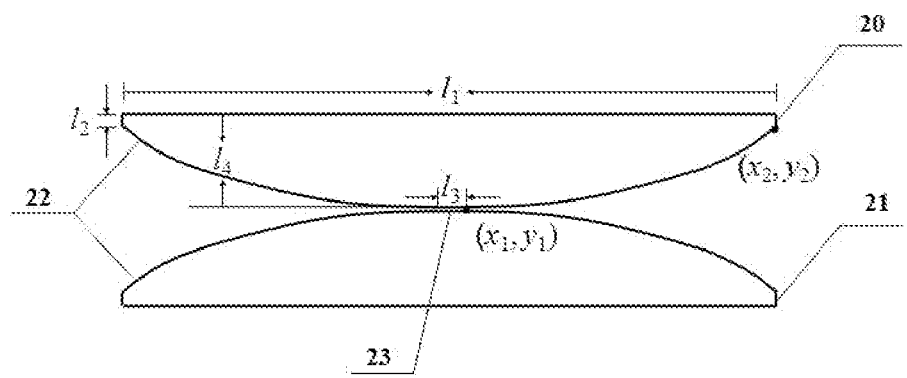
FIG. 2 is a schematic diagram of a horn-like oxygen-free copper metal plate waveguide in a transient-state THz spectrometer for detecting cells and biological macromolecules of the disclosure.

Because a TEM mode propagated in the metal slab waveguide has excellent characteristics such as low loss, no cut-off frequency and negligible group velocity dispersion, the slab waveguide 8 in the disclosure is a horn-like structure made of an oxygen-free copper metal material, and may transform the terahertz wave in the free space into the TEM mode propagated in the oxygen-free copper metal slab waveguide. In addition, the disclosure also performs a reasonable design on the horn-like gradient waveguide, thereby the coupling efficiency is guaranteed to meet the research of transient dynamics, and a specific structure of the horn-like oxygen-free copper metal slab waveguide is as follows:

As shown in FIG. 2, the slab waveguide 8 comprises axial-symmetrically disposed slab upper waveguide 20 and slab lower waveguide 21. It may be understood that the symmetrically disposed slab upper waveguide 20 and slab lower waveguide 21 refer to mirror symmetry of the slab upper waveguide 20 and the slab lower waveguide 21 in three dimensions, a symmetry axis is located on a symmetry plane, and an extension direction of the symmetry axis is a propagation direction of the terahertz wave. A gap between the slab upper waveguide 20 and the slab lower waveguide 21 d=50 µm-400 µm, the gap of the slab lower waveguide 21 is provided with a pseudo surface plasmon chip 23, the slab upper waveguide 20, the slab lower waveguide 21 and the pseudo surface plasmon chip 23 loaded in the gap of the slab lower waveguide 21 forms a horn-like gradient structure 22 together. The above pseudo surface plasmon chip 23 loaded in the gap of the slab lower waveguide 21 may be understood that the pseudo surface plasmon chip 23 is loaded on a surface, located at the gap, of the slab lower waveguide 21, it is designed that an overall length of the slab waveguide 8 I1=210 mm-310 mm, a distance from an upper edge of a horn port of the horn-like gradient structure 22 to an upper edge of the slab waveguide 8 I2=2 mm-2.5 mm, a propagation length of the parallel slab waveguide 8 I3=10 mm-20 mm, a distance from a lower edge of the horn port of the horn-like gradient structure 22 to an upper edge of the slab waveguide 8 I4=5 mm-10 mm, and one end point of the horn port of the horn-like gradient structure 22 is set as (x1, y1)=(0, 0), then the other end point (x2, y2)=((I1−I3)/2, I4), it is set that a smooth change trend of the waveguide horn port (namely the horn port of the horn-like gradient structure 22) α=0.0125 mm-0.02 mm.

A gradual change y (change trend) and a shape of the horn port of the horn-like gradient structure 22 are obtained by Formula (1):

Formula (1)

In the formula: x1<x<x2, y represents the change trend of the horn-like gradient structure 22, $$C_1 = \frac{y_2 - y_1}{e^{\alpha x_2} - e^{\alpha x_1}}, C_2 = \frac{y_1 e^{\alpha x_2} - y_2 e^{\alpha x_1}}{e^{\alpha x_2} - e^{\alpha x_1}},$$

and α represents the smooth change trend of the waveguide horn port, it determines the shape of the horn port (namely the horn port of the horn-like gradient structure 22), and (x1, y1) and (x2, y2) are two end points of the horn port respectively.

While the structure shown in FIG. 2 is used, through the use of the horn-like gradient structure 22, the terahertz wave in the free space may be transformed into the TEM mode propagated in the oxygen-free copper metal slab waveguide, the coupling efficiency thereof is as high as 80.5% in actual testing. At the same time, due to a smaller parallel plate spacing d in the oxygen-free copper metal plate waveguide, a TE mode and a TM mode have a higher cut-off frequency during a transmission process, so that only TEM mode transmission is supported within a certain low frequency range, thereby pulse splitting, caused by color dispersion and interference between the modes, of the terahertz pulse in the parallel slab waveguide is improved, and it is more suitable for a single measurement with a limited measurement time window; and finally, the small spacing d may achieve a local field enhancement effect of an electromagnetic field, thereby interaction between light and substance is more adequate, and it is beneficial to measurement of a trace sample.

Figure 3:
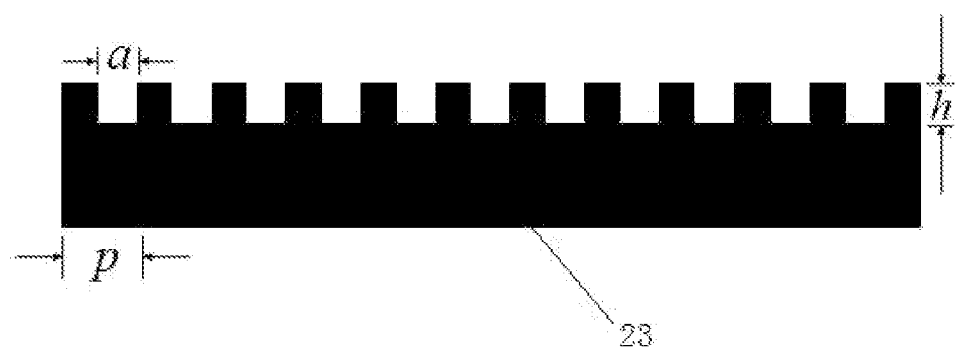
FIG. 3 is a schematic diagram of a pseudo surface plasmon chip of a grating structure in a transient-state THz spectrometer for detecting cells and biological macromolecules of the disclosure.

As shown in FIG. 3, an opening width of a grating of the pseudo surface plasmon chip 23 of the grating structure α=15 μm-40 μm, a period of the grating p=30 μm-80 μm, and an opening depth of the grating h=15 μm-40 μm. The disclosure is capable of enhancing the interaction between the terahertz wave and electrons in the metal by using the pseudo surface plasmon chip 23 of the grating structure, so that the free electrons on the surface of the oxygen-free copper metal generate a physical phenomenon of collective oscillation under the action of the terahertz wave, this phenomenon is called as surface plasmon. Because the electric field of the surface plasmon is bound to the metal surface and decays exponentially along the vertical direction, it has good field binding and enhancement effects and may be used for detection of trace water-containing biological samples.

In the disclosure, the nonlinear photoconductive antenna 6 is used as a terahertz radiation source, and the CCD camera 19 is used to receive single probe light containing terahertz wave information to achieve the single measurement. Because the blazed grating 10 makes the probe light pulse generate wavefront tilt, and then it is modulated by the nonlinear photoconductive antenna 6, finally a single detection of the terahertz pulse is achieved, and an advantage of time efficiency in a detection process is obtained. Therefore, a single measurement system may be used to detect some irreversible change processes such as a material damage, a chemical reaction, a phase distortion, and an ultra-fast process.

The disclosure is capable of, through the use of the horn-like gradient structure, transforming the terahertz wave in the free space into the TEM mode propagated in the oxygen-free copper metal slab waveguide, the coupling efficiency thereof is as high as 80.5% in actual testing. At the same time, due to a smaller parallel plate spacing d in the oxygen-free copper metal plate waveguide, a TE mode and a TM mode have a higher cut-off frequency during a transmission process, so that only TEM mode transmission is supported within a certain low frequency range, thereby pulse splitting, caused by color dispersion and interference between the modes, of the terahertz pulse in the parallel slab waveguide is improved, and it is more suitable for a single measurement with a limited measurement time window; and finally, the small spacing d may achieve a local field enhancement effect of an electromagnetic field, thereby interaction between light and substance is more adequate, and it is beneficial to measurement of a trace sample.

The disclosure accurately provides a structural parameter of the pseudo surface plasmon chip of the grating structure, it is used to adjust the pseudo surface plasmon color dispersion in the terahertz frequency band, the field in the vertical direction may be constrained in a sub-wavelength order, the interaction between the light and the substances is enhanced, while a propagation form of the terahertz wave is changed, and the effect of the water vapor absorption is reduced, so it is beneficial to the measurement of the trace water-containing samples, and finally, through experimental detection, the detection of the biological water-containing sample of which the molar mass concentration is the femtomolar level is achieved.

What is claimed is:

1. A transient-state THz spectrometer for detecting cells and biological macromolecules, wherein the transient-state THz spectrometer comprises a femtosecond laser amplifier, a femtosecond laser output by the femtosecond laser amplifier is divided into two beams of pump light and probe light after passing through a beam splitter of which a transmission-reflection ratio is 7:3, the pump light is focused to irradiate a gap between electrodes of a nonlinear photoconductive antenna and emit a terahertz wave after successively passing through a half wave plate, a silver-plated reflector and a first lens, the obtained terahertz wave forms a terahertz wave collineation after successively passing through a second lens, a slab waveguide, a third lens and a ITO film, the terahertz wave collineation and the probe light form a probe light collineation of wavefront tilt which is perpendicularly incident on a ZnTe crystal and detected and recorded by using a CCD camera.

2. The transient-state THz spectrometer for detecting the cells and the biological macromolecules according to claim 1, wherein the probe light obtained by the beam splitter successively passes through a blazed grating and a silver-plated reflector and is reflected to a first polarizer, and then focused by a fourth lens and passes through the ITO film to form the probe light collineation of wavefront tilt, and an angle of the blazed grating is 66.44° deviated from a vertical direction.

3. The transient-state THz spectrometer for detecting the cells and the biological macromolecules according to claim 2, wherein a line density of the blazed grating is 1200 lines/mm, and a blaze wavelength is 800 nm.

4. The transient-state THz spectrometer for detecting the cells and the biological macromolecules according to claim 1, wherein one side, away from the ITO film, of the ZnTe crystal is successively provided with a quarter wave plate, a fifth lens and a second polarizer, the probe light amplified by the fifth lens passes through the second polarizer and is imaged to the CCD camera.

5. The transient-state THz spectrometer for detecting the cells and the biological macromolecules according to claim 1, wherein the slab waveguide is a horn-like structure made of an oxygen-free copper metal material.

6. The transient-state THz spectrometer for detecting the cells and the biological macromolecules according to claim 5, wherein the slab waveguide comprises axial-symmetrically arranged slab upper waveguide and slab lower waveguide, a gap between the slab upper waveguide and the slab lower waveguide d=50 μm-400 μm, the gap of the slab lower waveguide is provided with a pseudo surface plasmon chip, the slab upper waveguide, the slab lower waveguide and the pseudo surface plasmon chip loaded in the gap of the slab lower waveguide form a horn-like gradient structure together.

7. The transient-state THz spectrometer for detecting the cells and the biological macromolecules according to claim 6, wherein an overall length of the slab waveguide $I_1$=210 mm-310 mm, a distance from an upper edge of a horn port of the horn-like gradient structure to an upper edge of the slab waveguide $I_2$=2 mm-2.5 mm, a propagation length of the slab waveguide $I_3$=10 mm-20 mm, a distance from a lower edge of the horn port of the horn-like gradient structure to an upper edge of the slab waveguide $I_4$=5 mm-10 mm, a smooth change trend of the horn port α=0.0125 mm-0.02 mm, and two end points of the horn port are respectively $(x_1, y_1)$ and $(x_2, y_2)$, it is set $(x_1, y_1)$=(0, 0); then $(x_2, y_2)$=$(I_1-I_3/2, I_4)$.

8. The transient-state THz spectrometer for detecting the cells and the biological macromolecules according to claim 6, wherein an opening width of a grating of the pseudo surface plasmon chip a=15 μm-40 μm, a period of the grating p=30 μm-80 μm, and an opening depth of the grating h=15 μm-40 μm.

9. The transient-state THz spectrometer for detecting the cells and the biological macromolecules according to claim 6, wherein the horn-like gradient structure is used to transform the terahertz wave in the free space into a TEM mode propagated in the slab waveguide, and the coupling efficiency thereof is 80.5%.

10. The transient-state THz spectrometer for detecting the cells and the biological macromolecules according to claim 1, wherein the femtosecond laser amplifier is a Ti sapphire regenerative amplifier, a laser repetition frequency of the femtosecond laser amplifier is 1 Hz-1000 Hz, average power is 5 W, and a pulse width is 100 fs.

11. A transient-state THz spectrometer for detecting cells and biological macromolecules, comprising:
   a femtosecond laser amplifier, used to output a femtosecond laser;
   a beam splitter, used to divide the femtosecond laser into two beams of pump light and probe light;
   a half wave plate, a silver-plated reflector, a first lens and a nonlinear photoconductive antenna, wherein the first lens is used to focus the pump light successively passing through the half wave plate and the silver-plated reflector to irradiate a gap between electrodes of the nonlinear photoconductive antenna, and the nonlinear photoconductive antenna is used to emit a terahertz wave;
   a second lens, a slab waveguide, a third lens and an ITO film, used to form a terahertz wave and probe light collineation after enabling the terahertz wave to successively pass and perpendicularly incident on a ZnTe crystal; and
   a CCD camera, used to detect and record the probe light incident on the ZnTe crystal and carrying information of the terahertz wave.

12. The transient-state THz spectrometer for detecting the cells and the biological macromolecules according to claim 11, wherein the transient-state THz spectrometer further comprises:
   a silver-plated reflector, a first polarizer and a fourth lens, the silver-plated reflector is used to reflect the probe light passing through the blazed grating to the first polarizer, the fourth lens is used to focus the probe light passing through the first polarizer, the ITO film is used to enable the focused probe light to pass and reflect the terahertz wave so as to form the probe light of wavefront tilt which is collinear with the terahertz wave, and an angle of blazed grating is 66.44° deviated from a vertical direction.

13. The transient-state THz spectrometer for detecting the cells and the biological macromolecules according to claim 12, wherein a line density of the blazed grating is 1200 lines/mm, and a blaze wavelength is 800 nm.

14. The transient-state THz spectrometer for detecting the cells and the biological macromolecules according to claim 11, wherein the transient-state THz spectrometer further comprises a quarter wave plate, a fifth lens and a second polarizer, the fifth lens and the second polarizer are disposed at one side, away from the ITO film, of the ZnTe crystal and successively arranged along a direction away from the ITO film, the fifth lens is used to beam-expand the probe light which pass by, and the beam-expanded probe light is imaged to the CCD camera after passing through the second polarizer.

15. The transient-state THz spectrometer for detecting the cells and the biological macromolecules according to claim 11, wherein the slab waveguide is a horn-like structure made of an oxygen-free copper metal material.

16. The transient-state THz spectrometer for detecting the cells and the biological macromolecules according to claim 15, wherein the slab waveguide comprises axial-symmetrically arranged slab upper waveguide and slab lower waveguide, a gap between the slab upper waveguide) and the slab lower waveguide d=50 μm-400 μm, a surface, located at the gap, of the slab lower waveguide is provided with a pseudo surface plasmon chip, the slab upper waveguide, the slab lower waveguide and the pseudo surface plasmon chip loaded in the gap form a horn-like gradient structure together.

17. The transient-state THz spectrometer for detecting the cells and the biological macromolecules according to claim 16, wherein an overall length of the slab waveguide $I_1$=210 mm-310 mm, a distance from an upper edge of a horn port of the horn-like gradient structure to an upper edge of the slab waveguide $I_2$=2 mm-2.5 mm, a propagation length of the slab waveguide $I_3$=10 mm-20 mm, a distance from a lower edge of the horn port of the horn-like gradient structure to an upper edge of the slab waveguide $I_4$=5 mm-10 mm, a smooth change trend of the horn port α=0.0125 mm-0.02 mm, and two end points of the horn port are respectively $(x_1, y_1)$ and $(x_2, y_2)$, it is set $(x_1, y_1)$=(0, 0); then $((I_1-I_3)/2, I_4)$.

18. The transient-state THz spectrometer for detecting the cells and the biological macromolecules according to claim 16, wherein an opening width of a grating of the pseudo surface plasmon chip a=15 μm-40 μm, a period of the grating p=30 μm-80 μm, and an opening depth of the grating h=15 μm-40 μm.

19. The transient-state THz spectrometer for detecting the cells and the biological macromolecules according to claim 16, wherein the horn-like gradient structure is used to transform the terahertz wave in the free space into a TEM mode propagated in the slab waveguide, and the coupling efficiency thereof is 80.5%.

20. The transient-state THz spectrometer for detecting the cells and the biological macromolecules according to claim 11, wherein the femtosecond laser amplifier is a Ti sapphire regenerative amplifier, a laser repetition frequency of the femtosecond laser amplifier is 1 Hz-1000 Hz, average power is 5 W, and a pulse width is 100 fs.

* * * * *